US008801771B2

(12) United States Patent
Schmiedl

(10) Patent No.: US 8,801,771 B2
(45) Date of Patent: Aug. 12, 2014

(54) ENDOPROSTHESIS

(75) Inventor: Robert Schmiedl, Hirschaid (DE)

(73) Assignee: Biotronick VI Patent AG, Baar (CH)

( * ) Notice: Subject to any disclaimer, the term of this patent is extended or adjusted under 35 U.S.C. 154(b) by 203 days.

(21) Appl. No.: 12/955,829

(22) Filed: Nov. 29, 2010

(65) Prior Publication Data
US 2011/0190869 A1      Aug. 4, 2011

Related U.S. Application Data

(60) Provisional application No. 61/285,549, filed on Dec. 11, 2009.

(51) Int. Cl.
*A61F 2/86* (2013.01)
*A61F 2/90* (2013.01)

(52) U.S. Cl.
CPC ... *A61F 2/86* (2013.01); *A61F 2/90* (2013.01); *A61F 2220/0075* (2013.01); *A61F 2250/0012* (2013.01); *A61F 2250/0018* (2013.01)
USPC ......................................... 623/1.15; 623/1.16

(58) Field of Classification Search
CPC ..... A61F 2/86; A61F 2250/0018; A61F 2/90; A61F 2220/0075; A61F 2250/0012
USPC ............. 623/1.1, 1.12, 1.15, 1.16, 1.17, 1.18, 623/1.19, 1.2, 1.32, 1.33, 23.7, 1.3
See application file for complete search history.

(56) References Cited

U.S. PATENT DOCUMENTS

| | | | | |
|---|---|---|---|---|
| 5,868,781 | A * | 2/1999 | Killion | 623/1.15 |
| 7,704,275 | B2 * | 4/2010 | Schmid et al. | 623/1.16 |
| 7,828,836 | B2 * | 11/2010 | Besselink | 623/1.15 |
| 8,092,514 | B1 * | 1/2012 | Khosravi et al. | 623/1.15 |
| 2001/0016770 | A1 * | 8/2001 | Allen et al. | 623/1.15 |
| 2004/0093072 | A1 * | 5/2004 | Pappas et al. | 623/1.15 |

(Continued)

FOREIGN PATENT DOCUMENTS

| | | |
|---|---|---|
| EP | 0 827 725 A1 | 3/1998 |
| EP | 1 642 551 A1 | 4/2006 |
| WO | WO 2007/005800 A1 | 1/2007 |

OTHER PUBLICATIONS

European Search Report for EP 10 19 1148.

*Primary Examiner* — David Isabella
*Assistant Examiner* — Suba Ganesan
(74) *Attorney, Agent, or Firm* — Biotech Beach Law Group PC; Raymond Wagenknecht

(57) ABSTRACT

An endoprosthesis, particularly an intraluminal endoprosthesis, having a basic structure that is preferably configured in the shape of a hollow cylinder, preferably configured as a basic lattice. In the expanded state, an inner volume enclosed by the basic structure can be changed by means of the elasticity of the basic structure, where the basic structure can assume a normal state and a state of significant compression, with regard to its compression behavior, for further improvement of the healing progression when using an endoprosthesis according to the invention, where in the state of significant compression, the elasticity of the basic structure is significantly reduced as compared with the elasticity in the normal state. The state of significant compression is characterized by the fact that an inside diameter threshold value of the basic structure is not reached, or that a compression pressure threshold value is exceeded. In this connection, the inside diameter threshold value preferably amounts to about 75% of a nominal inside diameter, or the compression pressure threshold value preferably amounts to about 0.2 bar.

20 Claims, 8 Drawing Sheets

(56) References Cited

U.S. PATENT DOCUMENTS

| | | | |
|---|---|---|---|
| 2004/0249442 A1* | 12/2004 | Fleming et al. | 623/1.15 |
| 2005/0070995 A1* | 3/2005 | Zilla et al. | 623/1.32 |
| 2006/0020325 A1* | 1/2006 | Burgermeister et al. | 623/1.16 |
| 2006/0064160 A1* | 3/2006 | Gerold et al. | 623/1.38 |
| 2007/0233233 A1* | 10/2007 | McGovern et al. | 623/1.15 |
| 2008/0051866 A1 | 2/2008 | Chen et al. | |

* cited by examiner

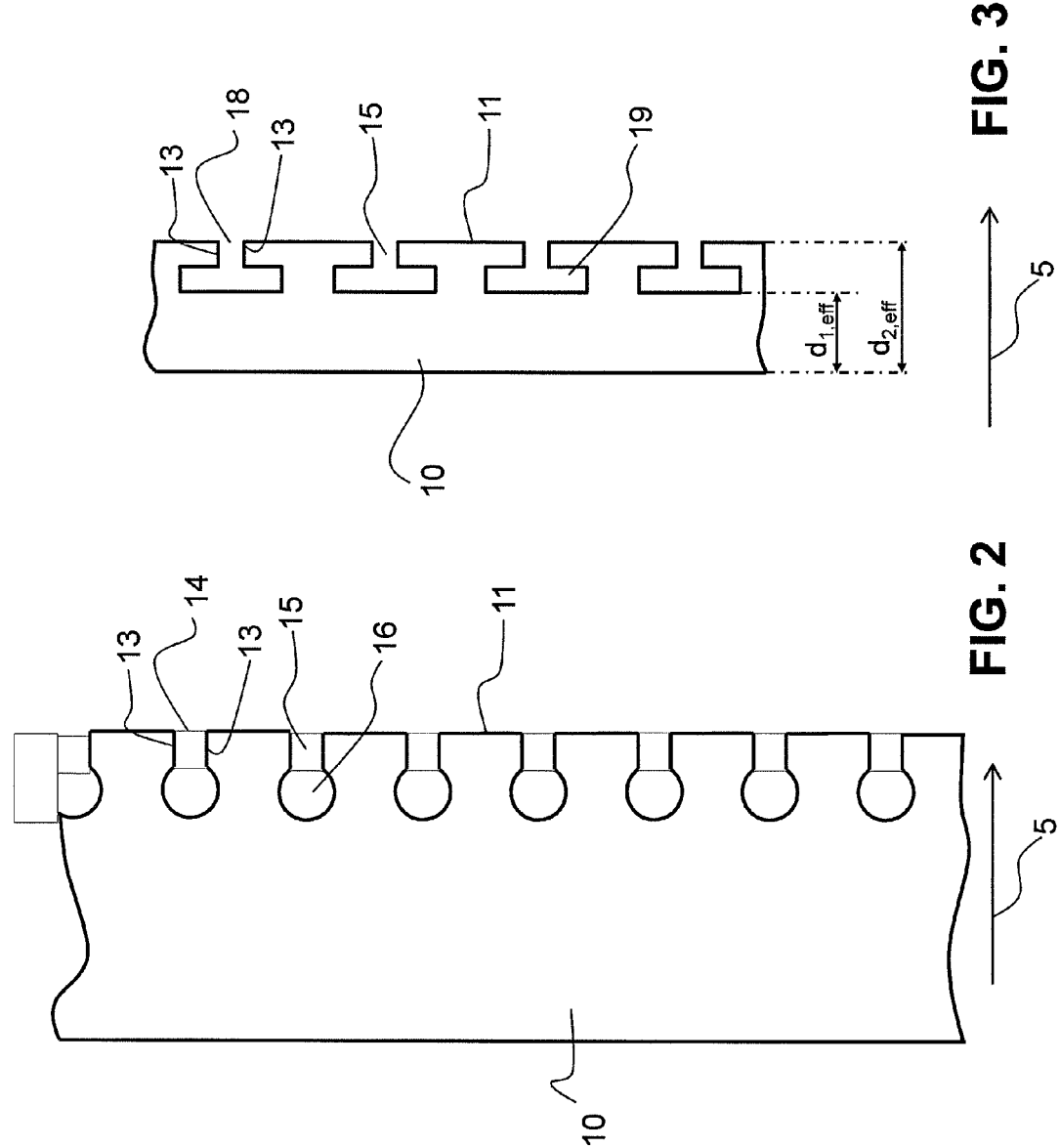

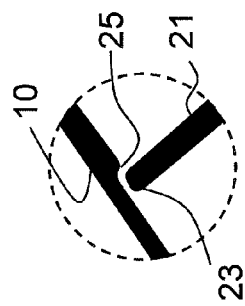
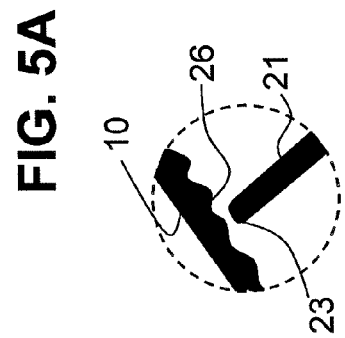
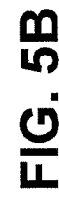
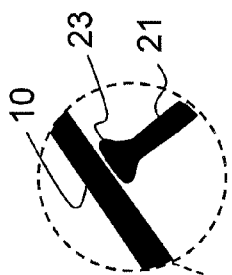
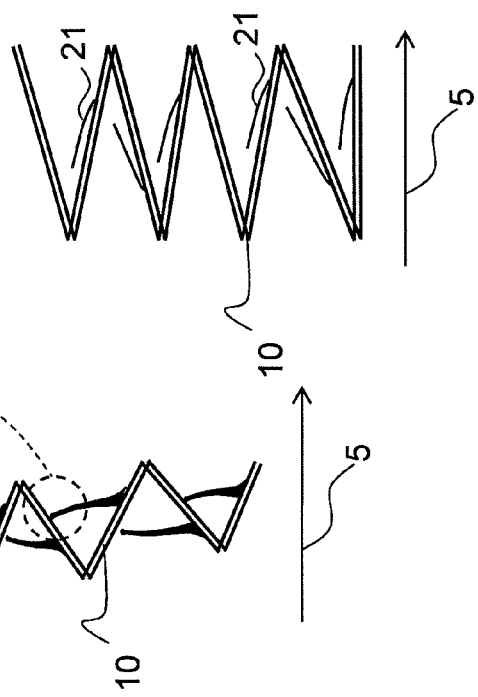
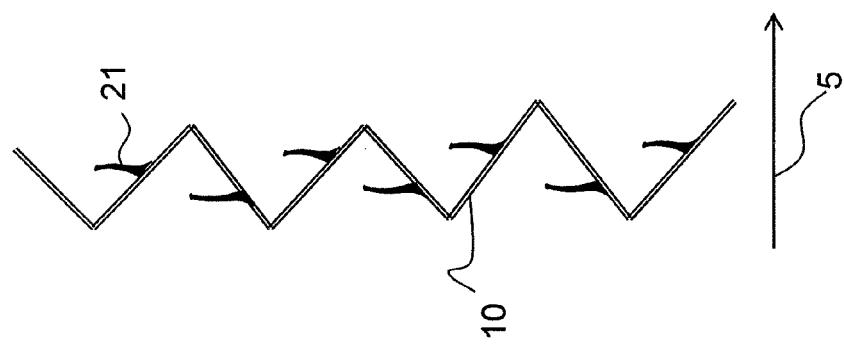

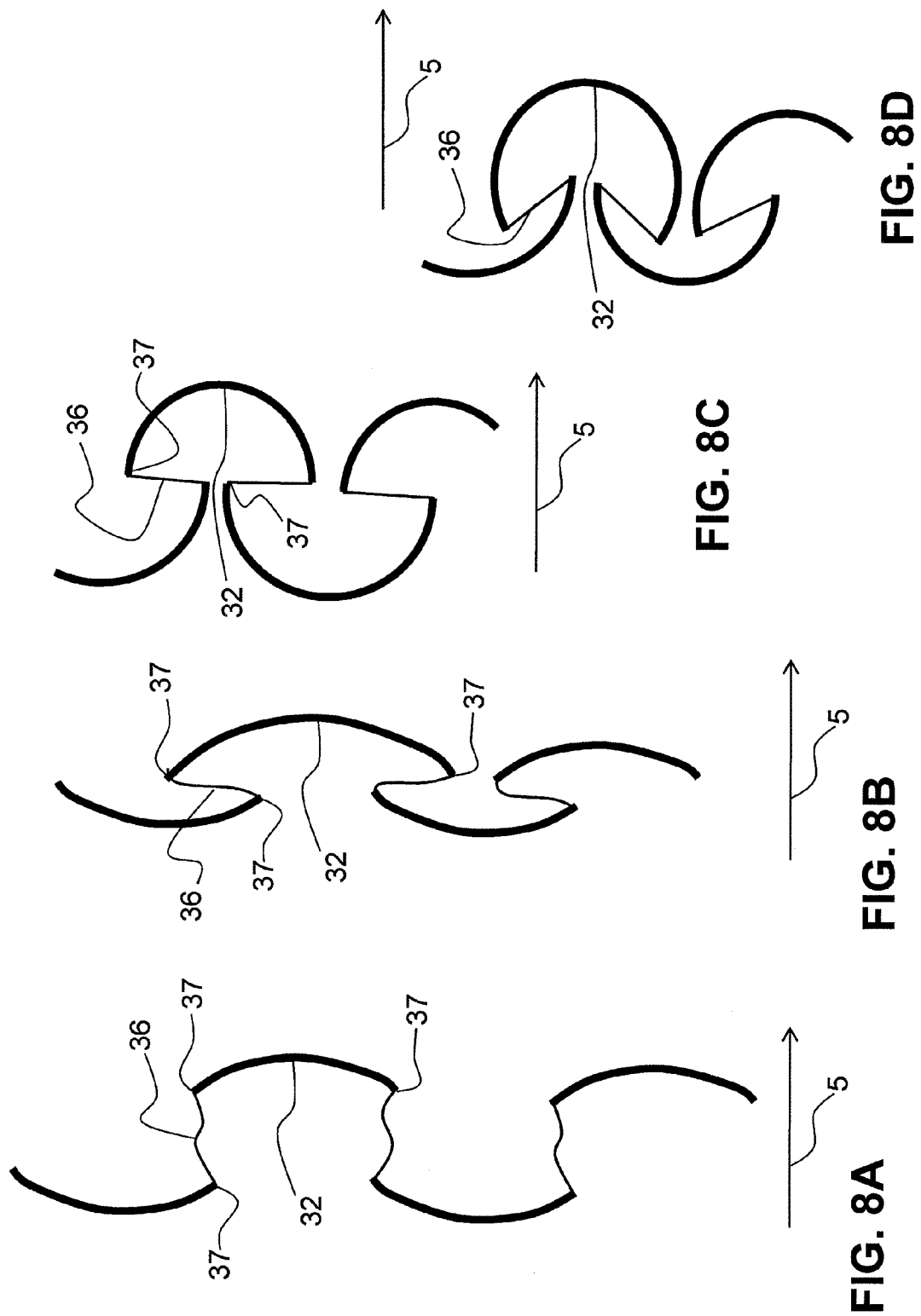

ENDOPROSTHESIS

CROSS REFERENCE TO RELATED APPLICATIONS

This invention claims benefit of priority to U.S. patent application Ser. No. 61/285,549, filed on Dec. 11, 2009; the contents of which are herein incorporated by reference in their entirety.

TECHNICAL FIELD

The invention relates to an endoprosthesis, particularly an intraluminal endoprosthesis, having a basic structure preferably configured in the shape of a hollow cylinder, which is preferably configured as a basic lattice.

BACKGROUND OF THE INVENTION

Very frequently used representatives of endoprostheses are stents (endovascular prosthese) that are used for the treatment of stenoses (vascular constrictions). Stents generally have a basic structure in the shape of a hollow cylinder or tube that is open at both ends. The endoprosthesis is inserted into the blood vessel or body part to be treated, and serves to support it and/or hold it open. Stents usually assume one of two states, namely a compressed state with a small diameter, and an expanded state with a larger diameter. In the compressed state, the stent can be introduced into the blood vessel to be supported, by means of a catheter, and positioned at the location to be treated. For this purpose, the stent is frequently crimped onto a catheter. At the location of treatment, the stent is then dilated, for example by means of a balloon catheter, or makes a transition into the expanded state (when a shape memory metal is used as the stent material) by means of being heated in the blood, above its critical temperature.

The reason for the benefit of implantation of endoprostheses into blood vessels is the greater primary gain in lumen that is produced by the inner volume of the basic structure. It is true that an optimal vascular cross-section that is necessary for therapy success can be achieved by means of the use of such endoprostheses, but the permanent presence of such a foreign body induces a cascade of microbiological processes that can lead to the stent gradually becoming overgrown. For example, tiny injuries, tears, or dissections of the vascular wall are caused during contact of the endoprosthesis with the vascular wall during dilatation, i.e. during widening of the blood vessel, which generally heal without problems, but can lead to excrescences because of the cell growth that is triggered. The permanent presence of an implant also brings about processes that can lead to narrowing in the vascular cross-section, i.e. to restenosis.

For the reasons indicated above, it was previously the goal in the development of stents to achieve the greatest possible radial strength at the lowest possible recoil (elastic rebound). In this connection, radial strength is understood to be the internal resistance of the implant to forces that act radially and can bring about radial compression of the implant, in its expanded state. In this connection, the radial strength can be expressed quantitatively by stating a collapse pressure. In this connection, the compression takes place suddenly when the collapse pressure is reached—the implant collapses.

In the reference EP 1 642 551 A1, an implant is described that is characterized by a lower radial strength than previously known implants. This is because it was determined that a lower radial strength is not only tolerable, particularly for biodegradable implants, for a great number of pathological vascular changes, but also leads to a clear improvement in the healing process. In the reference EP 1 642 551 A1, an implant is therefore proposed in which, proceeding from the expanded state, the cross-sectional area, i.e. the internal volume gradually decreases with an increasing pressure applied radially, until a specific, predetermined pressure value is exceeded. The known implant can therefore be constantly compressed up to an established limit value of the internal volume, i.e. the cross-sectional area. A further increase in the compression pressure does not lead to a further decrease in the internal volume or the cross-sectional area until the compression exceeds the collapse pressure. If the compression pressure is increased further, the implant will collapse. The behavior of such an implant leads to an improvement in the healing progression, but this does not always proceed in satisfactory manner.

SUMMARY OF THE INVENTION

It is therefore the task of the present invention to create an endoprosthesis that is even further improved, particularly with regard to the healing progression and the restenosis behavior.

The above task is accomplished by means of an endoprosthesis that has a basic structure preferably in the shape of a hollow cylinder, which assumes two states with regard to its compression behavior, namely a normal state and a state of significant compression. According to the invention, the basic structure has an elasticity, in the normal state, by means of which the internal volume enclosed by the basic structure can be elastically, reversibly changed. The state of significant compression is characterized in that the inside diameter of the basic structure, i.e. the available internal volume is significantly reduced by means of pressures that act radially from the outside. In this connection, the inside diameter lies below a diameter threshold value, or the compression pressure lies above a compression threshold value. According to the invention, the elasticity of the basic structure is significantly reduced in the state of significant compression, as compared with the elasticity in the normal state.

Up to now, an elastic rebound (recoil) of stents was always considered a disadvantage, since it reduces the available lumen. For this reason, until now designing stents was generally aimed at minimizing this recoil, as explained above, so that the stents were configured to be very rigid. Furthermore, stents are generally dimensioned to the maximal diameter of the reference vascular section during implantation, also in order not to restrict the blood flow.

In this configuration of stents, it is left out of consideration that a healthy blood vessel is held at a diameter that is smaller than its maximal diameter under normal physiological conditions, for by far most of the time, and that it is widened only when there is a need for greater blood flow. This means that a healthy blood vessel demonstrates a certain elasticity that it makes use of in the normal state, in order to implement desired amounts of blood flowing through.

Because of the normal physiological behavior described above, implantation of rigid stents that are dimensioned for the maximal diameter of the blood vessel means a constant local over-dimensioning of the blood vessel. This represents a known stimulus for local neointima formation, which can induce or reinforce restenosis.

Contrary to established opinion, a design principle for endoprostheses is therefore now being proposed, in which elastic changes in diameter in the normal state, within the scope of physiologically normal variations, are fundamentally allowed. In particular, the invention eliminates or at least reduces the disproportion between the diameter made available by the endoprosthesis and the diameter required for the flow of bodily fluid (e.g. blood) that is actually required (on average). In this connection, the design principles previously applied are supposed to be retained, namely that the endoprostheses: lie against the vascular wall; and keep a volume open that allows sufficient supply to the target area According to the invention, the endoprosthesis is supposed to react to radial compression as follows, proceeding from the expanded state.

In the normal state, elastic rebound is permitted over a large range (in this connection, large means that the rebound corresponds to the magnitude of physiological lumen variations, e.g. 20%), where the radial forces required for deformation are supposed to correspond to those of healthy vascular musculature.

In the state of significant compression, a behavior with clearly reduced elasticity, all the way to rigid behavior, is supposed to be implemented as soon as the diameter has been reduced to a stenosis that could potentially limit flow. In this connection, "rigid" means that the endoprosthesis demonstrates a supporting force that can withstand a vascular spasm.

By means of such an endoprosthesis according to the invention, a significant stimulus for neointima formation will be eliminated or at least clearly weakened. Lesions treated with such an endoprosthesis are therefore less susceptible to restenosis.

Preferably, the endoprosthesis according to the invention is configured in such a manner that irreversible failure of the basic lattice of the endoprosthesis only occurs in the state of significant compression, at a further increase in the compression pressure up to a value above the collapse pressure.

In a preferred exemplary embodiment, the endoprosthesis according to the invention is implemented by means of a shape memory metal alloy, for example nitinol. Such an alloy is already inherently characterized by a large elastic deformation range. Endoprostheses, particularly stents, made of a self-expanding memory metal furthermore lie reliably against the wall of the blood vessel that was treated.

The essentially slightly elastic to rigid behavior in the state of significant compression as well as the behavior in the normal state, according to the invention, is not, however, implemented solely by means of the material selection, but rather particularly by means of the configuration of the elements of the basic structure of the endoprosthesis, which will be presented below using some examples. In this connection, the transition in elasticity from the normal state to the state of significant compression can take place discontinuously (e.g. brought about by means of a stop or barrier) or preferably also continuously (e.g. brought about by means of rotation of lever arms).

Preferably, the endoprosthesis according to the invention possesses a so-called progressive behavior. This means that the spring force, i.e. the reactive or repulsive force formed by the basic structure during compression increases disproportionately with the path. This behavior is particularly observed in the state of significant compression. Fundamentally, continued elastic behavior, merely with a greatly increased spring constant, is in accordance with the invention in the case of compression beyond the "inner stop," i.e. in the state of significant compression.

In the force-free state, which is also covered by the normal state, the endoprosthesis according to the invention assumes its nominal diameter. This diameter corresponds to the diameter of a healthy reference vascular section at maximal medication-induced vasodilatation (e.g. by NO). The behavior of the endoprosthesis according to the invention in the case of radial compression in the normal state is oriented in accordance with the physiological properties of the target blood vessel, in each instance. Frequently, in the rest state, the blood vessel is narrower by approximately 20% to 25% as compared with the nominal diameter.

Narrowing of the blood vessel is brought about by means of a contraction in the vascular wall (media) against the resistance of the blood pressure. Guideline values for normal arterial blood pressure lie in the range of about 130 mbar to about 200 mbar (approximately 100 to 150 mm Hg) systolic and less than about 120 mbar (approximately 90 mm Hg) diastolic. In the normal state, it is therefore supposed to be possible to elastically bring about a reduction in the inside diameter of the endoprosthesis according to the invention by 20% to 25% as compared with the nominal diameter, on the basis of radial forces such as those brought about by physiological changes in the vascular wall tension. Accordingly, the preferred pressure range for the normal state is supposed to extend up to a compression pressure threshold value of about 200 mbar, preferably up to a compression pressure threshold value of 100 mbar, particularly preferably up to a compression pressure threshold value of 75 mbar. Above the stated compression pressure threshold value, the endoprosthesis according to the invention is in the state of significant compression.

If further compression of the endoprosthesis occurs, flow-reducing effects occur in the blood vessel being treated, which the endoprosthesis according to the invention must counter with an increased support effect. Preferably, a reasonable value for the extent of a further elastic compression that might still be tolerable results from the minimum diameter to be kept open, increased by a safety margin that takes a neointima that might have formed and/or a dilatation that is not radially symmetrical into account. In many cases, the reduction in diameter to be kept open can amount to approximately 50% of the diameter, with a reserve of approximately 25% having to be calculated in. Consequently, the state of significant compression can preferably be characterized in that the inside diameter is reduced to 75% of the nominal diameter. This means approximately the same thing as that the compression pressure exceeds the compression pressure threshold value indicated above.

In a preferred exemplary embodiment of the endoprosthesis according to the invention, its elastic resistance in the state of significant compression amounts to at least ten times the elastic resistance in the normal state. This configuration of the endoprosthesis according to the invention leads to the desired rigid behavior in the state of significant compression, and, as will be shown below, can easily be implemented by means of a corresponding arrangement of crosspieces and adaptation of the crosspiece widths of the elements of the basic structure, for example. In this connection, the elastic resistance is defined as the pressure to be externally applied in the radial direction, with reference to a change in diameter brought about by this pressure.

The endoprosthesis according to the invention is characterized, in a particularly preferred exemplary embodiment, in that forces introduced into the endoprosthesis in the state of significant compression bring about predominantly a single-axis stress state (tensile stress or compression) of at least a part of the elements of the basic structure of the endoprosthesis. With such a configuration of the endoprosthesis according to the invention, it is possible to implement the desired rigid behavior of the endoprosthesis in the state of significant compression in very simple manner. Furthermore preferably, the forces introduced into the endoprosthesis in the normal state predominantly bring about bending stress of elements of the endoprosthesis, by means of which the desired elastic behavior of the endoprosthesis can be brought about.

In another exemplary embodiment, the basic structure has means that lie against one another if the specific, predetermined inside diameter threshold value is not reached.

In a preferred exemplary embodiment, the means are configured as a notch or multiple notches (slits) spaced apart from one another in crosspieces of the basic structure, whose wall sections, which lie opposite one another, lie against one another when the radius of curvature of the crosspiece, in each instance, goes below a specific, predetermined value in the state of significant compression, in such a manner that they counteract any further reduction in the average radius of curvature of the crosspiece in question. In this exemplary embodiment, the notches are disposed on the inside of the crosspieces of the basic structure with regard to the curvature. In the event of compression, the crosspieces with a notch/notches are curved further.

In a variant of the previously mentioned exemplary embodiment, the means are configured as a notch or multiple notches (slits) spaced apart from one another in crosspieces of the basic structure, whose wall sections, which lie opposite one another, lie against one another when the radius of curvature of the crosspiece, in each instance, goes above a specific, predetermined value in the state of significant compression, in such a manner that they counteract any further increase in the average radius of curvature of the crosspiece in question. In this exemplary embodiment, the notches are disposed on the outside of the crosspieces of the basic structure with regard to the curvature. In this variant, the crosspieces with a notch/notches are straightened in the event of compression.

In the case of both variants of an exemplary embodiment mentioned above, the notch or notches can have a V shape, a U shape, a rectangular shape or any other shape, as well as a complicated, composite shape. In connection with the shape of the notches, the shape of the bottom of the notches is less important; what is important is that the walls of the notches come into contact with one another at a specific, predetermined distance from the bottom, in the state of increased compression.

This exemplary embodiment with notch or notches includes a simple implementation of two states of the compression behavior of endoprostheses, one with great elasticity and one with a comparatively clearly lower elasticity. In the normal state, the effective diameter of the crosspiece, in each instance, is clearly reduced by the notch or notches, so that bending of the crosspiece is easily possible and thus the desired elasticity is achieved. The state of significant compression is characterized by a "stop" when wall sections of the notches or slits that lie opposite one another come to lie against one another. Since the side wall sections are lying against one another, the effective diameter of the crosspiece, in each instance, is increased by the length (depth) of the notch, and the force that is required for deformation clearly increases.

In another exemplary embodiment, the means are configured as a contact element that projects away from the crosspiece, in each instance, and runs essentially crosswise to the longitudinal direction of the endoprosthesis, preferably as an essentially rod-shaped pin or mandrel, where each contact element lies against or comes up against a crosspiece that lies opposite it, in each instance, when the specific, predetermined inside diameter threshold value is not reached. For this purpose, the ends of the contact elements that lie against the opposite crosspiece are preferably reinforced; in particular, they have a greater diameter than the rear section of the contact element that follows them. In a particularly preferred exemplary embodiment, a plurality of crosspieces has such a contact element, in each instance. Preferably, the pin or mandrel has a rectangular cross-section, which is easy to produce.

In order to guarantee defined impact or contact of the means in the state of significant compression, i.e. to prevent the contact elements from sliding off to the side of the opposite crosspiece, the means preferably have shape-fit means that form a shape fit in the state of significant compression. For example, a crosspiece that lies opposite the contact element can have notches or depressions. The corresponding end of the contact element can form a shape with such a notch or depression, in the contact position.

The exemplary embodiments described above, with notches in the crosspieces or contact elements, are example of the fact that forces introduced into the endoprosthesis in the state of significant compression predominantly bring about compression of elements of the basic structure. In the case of the exemplary embodiments discussed below, predominantly tensile stress of at least a part of the elements of the basic structure is brought about in the state of significant compression.

Since it can be technically difficult in the case of implantations in real stenoses, which are frequently asymmetrical or partially calcified, to reliably implement the stop in the event of compression of the endoprosthesis, or to hit it reliably, particularly if distances on the order of the mesh size of the basic structure are to be bridged, additional exemplary embodiments of the present invention will be explained in the following, which make do without means for making contact, i.e. stops.

Another disadvantage of solutions that contain a stop consists in that when two hard parts are pressed against one another, there is the risk of pinching tissue parts or vascular parts between them. In this connection, small blood vessels of the vascular wall for supplying the vascular wall (vasa vasorum) or other functionally important components such as the membrana elastica interna, for example, can be damaged. Injuries to such components can bring about an inflammation stimulus or internal hemorrhaging, or can promote migration.

In a stop-free exemplary embodiment of the endoprosthesis according to the invention, the basic structure has transverse crosspieces that run essentially transverse to the longitudinal direction of the endoprosthesis, which are preferably curved in the normal state, as well as longitudinal crosspieces that run essentially in the longitudinal direction, where the transverse crosspieces and the longitudinal crosspieces are connected with one another and are disposed alternately one behind the other in the circumference direction of the endoprosthesis. The transverse direction and the circumference direction run perpendicular to the longitudinal direction of the endoprosthesis. The longitudinal direction is parallel to the longitudinal axis of the endoprosthesis.

Parallel to a transverse crosspiece between two connection locations, in each instance, a restriction crosspiece is disposed, in each instance, which counteracts a further increase in the radius of curvature of the transverse crosspiece if the radius of curvature of the transverse crosspieces lies above a specific, predefined radius of curvature threshold value of the transverse crosspiece, i.e. in the state of significant compression. The restriction crosspiece therefore forms a restriction, in the state of significant compression, for further stretching of the transverse crosspiece, and thus prevents further compression of the endoprosthesis. Preferably, the restriction crosspiece is taut in the state of significant compression. When the maximal extension of each transverse crosspiece is reached, further compression forces are therefore introduced into the restriction crosspiece as tensile forces, thereby preventing further bending (curvature) of the transverse crosspieces. In this exemplary embodiment, the longitudinal crosspieces are preferably configured to be significantly more rigid with regard to bending deformation than the transverse crosspieces, so that the endoprosthesis can deform further elastically only very slightly in the state of significant compression, by means of deformation of the longitudinal crosspieces. This means that there is a clear difference in the elastic behavior between the two states. The restriction crosspiece preferably has such a small diameter that in the normal state, it does not have a significant influence on the bending deformation of the parallel transverse crosspiece, in each instance.

In the case of another stop-free embodiment variant, the basic structure has meshes that are formed by two transverse crosspieces that run essentially transverse to the longitudinal direction of the endoprosthesis, in each instance, which are connected with one another at their ends, where the two transverse crosspieces (e.g. in the interior of a mesh) are additionally connected by at least one connector crosspiece that runs essentially in the longitudinal direction of the endoprosthesis, which counteracts a further increase in the distance between the two transverse crosspieces in the region of the connector crosspiece, above a specific, predefined distance between the transverse crosspieces, i.e. in the state of significant compression. This exemplary embodiment also represents a simple possibility for introducing the compression forces that act from the outside in the state of significant compression particularly into the connector crosspieces, which run in the longitudinal direction, and thus limiting the elasticity of the basic structure.

It is furthermore preferred if the basic structure is formed by transverse crosspieces and restriction crosspieces that are alternately disposed transverse to the longitudinal direction of the endoprosthesis and connected with one another, where the transverse crosspieces run essentially transverse to the longitudinal direction in the normal state, and the restriction crosspieces run essentially in the longitudinal direction of the endoprosthesis in the normal state, at least in certain sections, and where furthermore, the restriction crosspieces can be rotated, with increasing compression, in such a manner that they run increasingly transverse to the longitudinal direction, where the elasticity of the restriction crosspieces decreases with increasing rotation, where in the normal state, the spring constant a of the transverse crosspieces is greater than the spring constant b of the restriction crosspieces, preferably a>10·b, and in the state of significant compression, the tensile strength of the restriction crosspieces is greater than the force required for bending of the transverse crosspieces. In the case of this exemplary embodiment, as well, the result is achieved, with simple means, that the forces introduced with increasing compression are absorbed by the restriction crosspieces, as tensile forces, to an ever increasing degree, where the restriction crosspieces increasingly rotate into the direction transverse to the longitudinal direction. After extension of the restriction crosspieces, further elasticity can only be achieved by means of bending of the transverse crosspieces, but these are configured to be comparatively rigid with regard to bending.

In the stop-free exemplary embodiments indicated above, it is advantageous if the restriction crosspieces or the connector crosspieces have a lesser width than the transverse crosspieces, where the width of the restriction crosspieces or the connector crosspieces is preferably less than ⅓ of the width of the transverse crosspieces. In this way, it is guaranteed that the connector crosspieces and restriction crosspieces, respectively, have no or only a very slight influence on the elastic behavior of the endoprosthesis, in the normal state.

It is furthermore advantageous if the basic structure, in a crimped state, has an inside diameter that is significantly smaller than the inside diameter of the endoprosthesis in the state of significant compression. In this way, it is possible to introduce the endoprosthesis into the body part to be treated, in simple manner, and to dilate it there. This treatment method has proven itself, since it can be carried out in minimally invasive manner and is cost-advantageous.

Other goals, characteristics, advantages, and application possibilities of the present invention are evident from the following description of exemplary embodiments, using figures. In this connection, all the characteristics described and/or shown in the figures form the object of the invention, by themselves or in any desired combination, even independent of how they are combined in individual claims or their antecedents.

BRIEF DESCRIPTION OF THE DRAWINGS

The figures listed below (except for FIGS. 9 to 11) are understood as a view from the side onto a section of the basic structure of the stent. They schematically show:

FIG. 2 depicts a section of a crosspiece of a second exemplary embodiment of an endoprosthesis according to the invention.

FIG. 3 depicts a section of a crosspiece of a third exemplary embodiment of an endoprosthesis according to the invention.

FIGS. 4A-D depict a section of the basic structure of a fourth exemplary embodiment of an endoprosthesis according to the invention.

FIGS. 5A-B depict two other variants of the configuration of a crosspiece relating to the fourth exemplary embodiment of an endoprosthesis according to the invention.

FIGS. 8A-D depict a section of the basic structure of a seventh exemplary embodiment of an endoprosthesis according to the invention.

DETAILED DESCRIPTION OF THE INVENTION

An endoprosthesis configured as a stent is composed of a lattice structure of crosspieces that run in the longitudinal direction 5 and in the transverse direction, which form a hollow cylindrical lattice body. The stents explained below, using the figures, each have such a lattice structure, where the transverse direction, i.e. circumference direction runs perpendicular to the longitudinal direction 5 (direction of the axis of the hollow cylinder), in each instance.

Figure 1B:
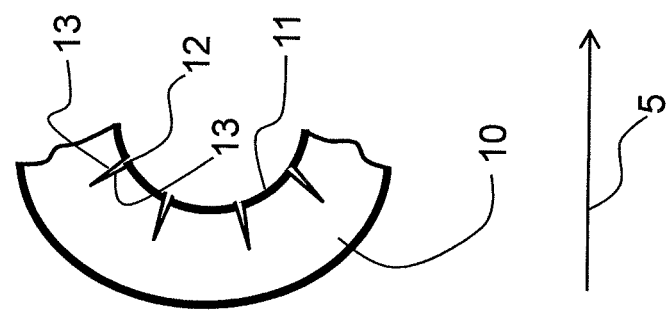
FIGS. 1A-B depict a section of a crosspiece of a first exemplary embodiment of an endoprosthesis according to the invention.
Figure 1A:
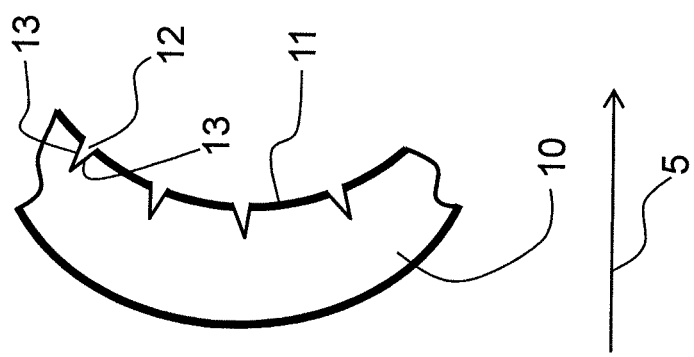

In FIGS. 1A-B, a crosspiece 10 of a stent, which runs essentially in the transverse direction, is shown, which is slightly curved in the normal state (see FIG. 1A). On the inside 11 of such a crosspiece, which has the smallest bending radius, V-shaped notches 12 have been introduced into the crosspiece 10, which reduce the effective crosspiece width in the normal state and thus bring about great elasticity of the crosspiece 10 when external compression forces act on it. In this connection, the compression forces generally act on the stent in the radial direction.

In the event of compression (see FIG. 1B), the bending radius of the crosspiece 10 is reduced. As a result, the V-shaped notches on the inside 11 are increasingly closed, and the side walls 13 of the notches 12, which lie opposite one another, approach one another to such an extent that they finally lie against one another. Therefore, in the state of significant compression, namely if a predetermined threshold value for the bending radius of the inside 11 of the crosspiece is not reached, a greater effective crosspiece width than in the normal state is implemented. The difference between the effective crosspiece widths in the normal state and in the state of significant compression is determined by the depth of the notches. As a result of the increased effective crosspiece width, an external compression force is countered with a greater elastic resistance. In the state of significant compression, the elasticity of the crosspiece is therefore clearly reduced, as compared with the normal state.

FIGS. 2 and 3 show other exemplary embodiments that differ from the embodiment shown in FIGS. 1A-B in the shape of their notches (slits).

In the exemplary embodiment shown in FIG. 2, notches 14 are provided, which are composed, in each instance, of a neck section 15 with straight side walls and an inner section 16 with side walls in the shape of a cylinder mantle. The cylindrical section 16 is disposed farther on the inside of the crosspiece 10, in each instance, than the neck section 15.

In the exemplary embodiment shown in FIG. 3, the cylindrical section 16 of the notches 14 shown in FIG. 2 is replaced with a block-shaped section 19. The block-shaped section 19 immediately follows the neck section 15, in each instance, in the case of the notch 18.

The exemplary embodiments shown in FIGS. 2 and 3 can also be called "dragon back" notches because of their shape. In FIG. 3, the effective diameters for bending of a crosspiece 10 are drawn in. In the normal state, the effective diameter $d_{1,eff}$, which extends from the side of the crosspiece 10 that lies opposite the notch 18 all the way to the front end of the notch 18, which lies furthest inside the crosspiece 10, is in effect. In the state of significant compression, the diameter $d_{2,eff}$, which corresponds to the total diameter of the crosspiece 10, is in effect.

The exemplary embodiments of an endoprosthesis according to the invention shown in FIGS. 2 and 3 can be better implemented, in practical terms, than the exemplary embodiment shown in FIGS. 1A-B. In this connection, the required ratio of the spring constants of the normal state as compared with the state of significant compression (namely, for example, by means of a suitable selection of the ratio $d_{1,eff}/d_{2,eff}$), and the required deformation path between the force-free normal state up to the state of significant compression (namely, for example, by means of a suitable selection of the ratio d(neck section)/$d_{2,eff}$) can be adjusted by means of a suitable selection of the geometric dimensions, independent of one another. In this connection, d(neck section) means the width of the notch, in the normal state, in the region of the neck section 15, in each instance.

The notches shown in FIGS. 1A to 3 can be introduced into the crosspieces preferably by means of laser cutting.

In FIGS. 4A to 8D, described below, basic structure segments are shown, cut open, which run along the circumference direction (transverse to the longitudinal direction 5 and can form the complete circumference of the stent or a part of it. Furthermore, the segments shown can be disposed in circular or helical shape.

In the fourth exemplary embodiment shown in FIGS. 4A-C, the basic structure segment is composed of crosspieces 10 that are disposed in a zigzag structure. Adjacent to the segment shown, other such segments are disposed. On a large number of crosspieces 10, according to the invention, essentially rod-shaped contact elements 21 in the form of pins are provided, which preferably project from the crosspiece 10, in each instance, at a specific, firmly predetermined angle. In FIG. 4A, a situation is shown in which the stent is present in the normal state. In this state, the stent can have an inside diameter of 4 mm, for example.

In the normal state, the basic structure of the stent is elastically deformable within broad limits. For example, elastic deformation is possible by means of S-shaped bending of the individual crosspieces 10 that are connected with one another. Compression by means of radial forces leads to the result that the stent diameter decreases, so that the adjacent crosspieces 10 move toward one another.

Such a movement and thus elastic compression are possible until the contact elements 21 that project away from the crosspieces, as shown in FIG. 4B, impact against the crosspiece 10 that lies opposite them, in each instance. An enlarged representation of the basic structure in the region in which a contact element 21 impacts against a crosspiece 10 that lies opposite it is shown in FIG. 4D. In this drawing, it can also be seen that in the preferred exemplary embodiment shown, the end 23 of the contact element 21 has a larger diameter as compared with the rear section of the contact element 21. In this way, the contact surface between the opposite crosspiece 10 and the contact element 21 upon impact is increased, so that reliable contact between contact element 21 and crosspiece 10 is formed. In this embodiment, it is advantageous if the angle formed between the contact element 21 and the crosspiece 10 lies at 90°, so that the contact element 21 is not pressed away sideways when compression occurs. This is because in the event of a deviation from 90°, there is always a transverse component of the force when the parts are pressed against one another, which causes the contact element 21 to slip away sideways.

In the state of significant compression shown in FIG. 4B, further elastic deformation of the basic structure is limited by the contact elements 21, which prevent a further reduction in the distance between adjacent crosspieces 10, i.e. a reduction in the angle enclosed between adjacent crosspieces 10. In the event of a further increase in the compression forces acting on the basic structure, these are absorbed by the contact elements 21 and lead to compression or bending of the contact elements 21. Since the elasticity constant increases, as compared with the elasticity constant of the structure formed solely from the crosspieces 10 and their connection locations, the elastic deformation of the basic structure is less in the state of significant compression.

In the state of significant compression, the stent diameter can amount to about 3 mm, for example.

FIG. 4C shows the state in which the stent has been crimped onto a catheter, for example. In this state, the stent is not yet dilated. In such a state, the stent can have a diameter of about 1.4 mm, for example. In the crimped state, the contact elements 21 lie against the crosspiece 10, in each instance, from which they project in the normal state, with at least part of their length. If the distances between adjacent crosspieces 10 are reduced, the contact element 21 therefore can no longer counteract any further compression.

Two other possibilities are shown using FIGS. 5A-B, as to how the impact of the contact element 21 on the opposite crosspiece 10 can be implemented. The goal of these possibilities is to increase the tolerance for variations in the precise orientation of the contact element 21 relative to the crosspiece 10, as these variations can be expected due to production tolerances and due to the influence of the surroundings at the implant location.

In the example shown in FIG. 5A, the crosspiece 10 has a step 25 or depression 25 in the contact region, against which the contact element 21 lies with shape fit in the state of significant compression. In this connection, the step 25 is configured in such a manner that it prevents displacement of the contact element 21 to the outside, i.e. in the direction that lies opposite the connection of the adjacent crosspieces 10. In this exemplary embodiment, it is advantageous if the angle between the contact element 21 and the crosspiece 10 is smaller than 90°, so that the contact element 21 is pressed into the step 25 when compression occurs. In this connection, a certain angle range below 90° can be tolerated; maximally to such an extent as the maximal incline of the edge of the step 25 determines. At an angle that lies too far below 90°, the contact element 21 would glide over the step 25; at an angle that clearly lies above 90°, it could slide off the step 25 without hindrance.

The exemplary embodiment shown in FIG. 5B represents a crosspiece having a wave-shaped structure formed at the surface, into the depressions 26 of which the contact element 21 can engage in the state of significant compression, with shape fit. Such a wave-shaped structure prevents displacement of the contact element 21 to the outside and the inside. In this embodiment, it is advantageous if the angle between the contact element 21 and the crosspiece 10 lies at about 90°, so that the contact element 21 is pressed into the depression 26 that it has hit when compression occurs. In this connection, certain deviations from 90° can also be tolerated; maximally to such an extent as the maximal incline of the depressions 26 determines. Only in the event of greater deviations would the contact element then slip sideways out of the depression.

FIGS. 6A-D show an exemplary embodiment of a stent whose basic structure is composed of longitudinal crosspieces 30 that run essentially in the longitudinal direction 5 and transverse crosspieces 32 that run essentially in the circumference direction (i.e. perpendicular to the longitudinal direction 5). A longitudinal crosspiece 30, in each instance, is disposed alternating with a transverse crosspiece 32, in the transverse direction, one behind the other. Parallel to every transverse crosspiece 32, a restriction crosspiece 34 is disposed, which is connected, at its ends, with an end point 35, in each instance, of the transverse crosspiece 32, in each instance.

Figure 6C:
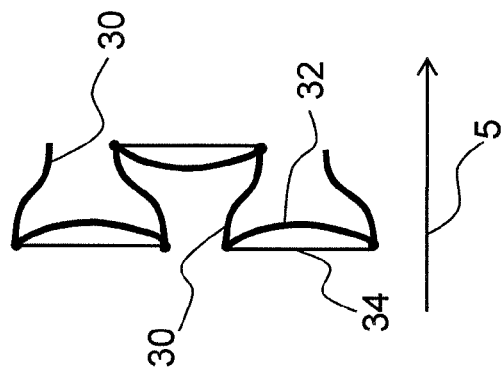
FIGS. 6A-D depict a section of the basic structure of a fifth exemplary embodiment of an endoprosthesis according to the invention in a view from the side.
Figure 6D:
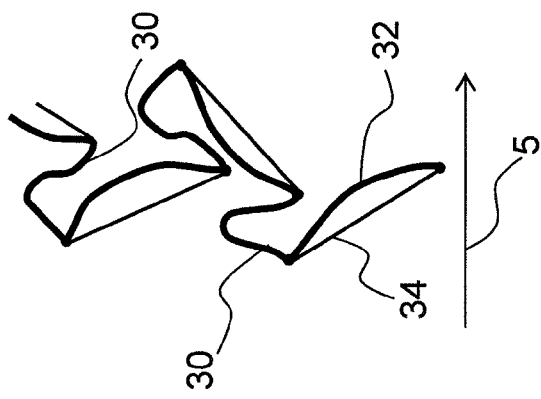
Figure 6B:
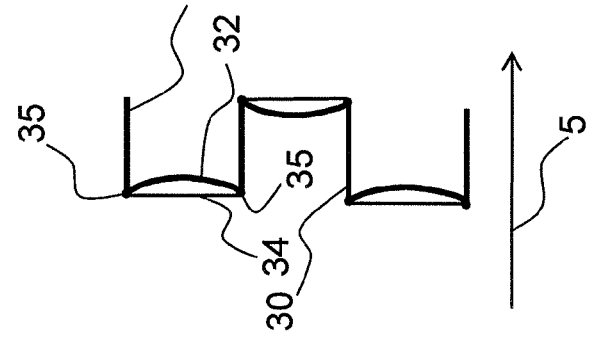
Figure 6A:
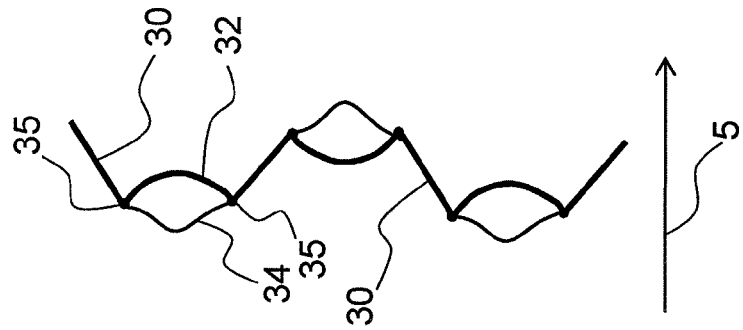

FIG. 6A shows a segment of the basic structure in the normal state. The elasticity of the basic structure is determined by the elasticity of the transverse crosspieces 32 and the longitudinal crosspieces 30, where preferably, the connection locations 35 between a transverse crosspiece 32 and a longitudinal crosspiece 30 are configured to be stable in angle, i.e. solid. In the event of compression of the stent according to the invention, first of all the transverse crosspieces 32, which have a smaller elasticity constant, are bent in such a manner that their radius of curvature is increased. This leads to the result that the distance between the end points 35 of the transverse crosspieces 32 increases, and each restriction crosspiece 34 runs increasingly straighter, i.e. more extended with an increasing compression, until the state of significant compression shown in FIG. 6B is present. In this state, the distance between the end points 35 of a transverse crosspiece 32 corresponds to the length of the parallel restriction crosspiece 34, in each instance, and the restriction crosspiece 34 is taut. In this state, additional compression forces are absorbed by the restriction crosspieces 34 as tensile forces, so that the elasticity of the basic structure is thereby limited. Part of the compression forces can also lead to bending of the longitudinal crosspieces 30, where the longitudinal crosspieces 30 are preferably configured to be clearly more rigid than the transverse crosspieces 32.

Preferably, the spring constant C of the restriction crosspieces 34 is smaller than the spring constant B of the transverse crosspiece 32, and this in turn is smaller than the spring constant A of the longitudinal crosspiece 30 (C<B<A, preferably C<<B<A), where all the spring constants mentioned represent spring constants against bending. In another exemplary embodiment, the longitudinal crosspiece 30 can also be configured in S shape. Furthermore, the angle enclosed by a longitudinal crosspiece 30 and a transverse crosspiece 32 at the connection location 35 does not necessarily have to amount to 90°, but rather can be configured to be slightly smaller than a right angle, or also clearly greater than 90°.

In the state of significant compression, greater elasticity is therefore prevented by means of stretching of the restriction crosspieces 34, so that the behavior of the stent in the event of further compression can be characterized as being hard. Further resilience occurs only by means of bending of the longitudinal crosspieces 30, which have a greater spring constant, however.

Using FIGS. 6C and 6D, two examples are presented that show a segment of the basic structure in the crimped state. It is clear that in the crimped state, the longitudinal crosspiece 30 is configured in S shape, so that a small inside diameter of the basic structure of the stent according to the invention can be implemented.

Figure 7C:
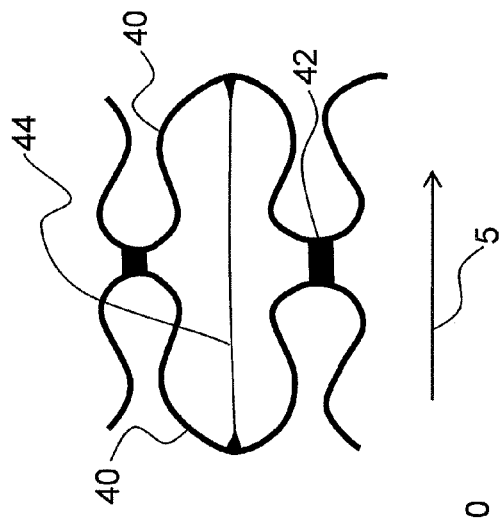
FIGS. 7A-C depict a section of the basic structure of a sixth exemplary embodiment of an endoprosthesis according to the invention.
Figure 7B:
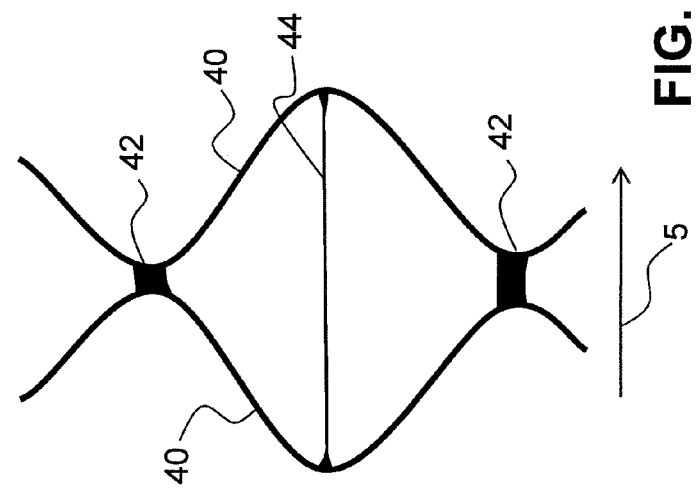
Figure 7A:
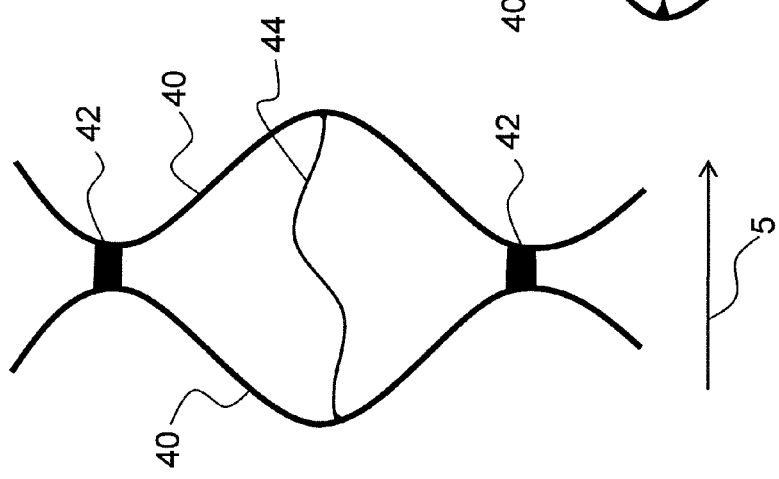

In the exemplary embodiment shown in FIGS. 7A-C, the basic structure of a stent according to the invention is composed of meshes that are formed by two transverse crosspieces 40 that run essentially in the transverse or circumference direction. The transverse crosspieces 40 are connected with one another at their ends, in each instance, by means of a connection location 42, in each instance. Approximately in the center region of each transverse crosspiece 40, a connector crosspiece 44 is disposed, which prevents further widening of the mesh, in each instance, and thus a further reduction of the inside diameter of the stent, in the event of increased compression.

FIG. 7A shows the normal state, in which the elasticity of the basic structure is determined by the elasticity of the crosspieces 40. If the distance between the two transverse crosspieces 40 exceeds a specific, predetermined threshold value in the event of further compression of the stent, then the connector crosspiece 44 is taut, i.e. extended. This state of significant compression is shown in FIG. 7B. In the event of further compression of the stent, the taut connector crosspieces 44 counter the applied forces, which are introduced into the connector crosspieces 44 as tensile forces, with resistance, so that the elasticity of the basic structure clearly decreases in this state.

In the state shown in FIG. 7C, the stent is crimped onto a catheter, where in this state, the sections of each transverse crosspiece 40 disposed above and below each connector crosspiece 44 are bent in S shape. By means of the deformation of the transverse crosspieces 40 indicated in FIG. 7C, the stent can assume a clearly smaller diameter in the crimped state than in the state of significant compression shown in FIG. 7B.

In conclusion, it should still be pointed out that the connection locations 42 of the stent shown in FIGS. 7A-C are configured to be stable in angle, i.e. rigid.

FIGS. 8A-D show another stop-free exemplary embodiment of a stent, in which the basic structure is composed of transverse crosspieces 32 that run essentially in the transverse direction, and longitudinal crosspieces 36 that run essentially in the longitudinal direction, which are disposed alternately, one behind the other, in the transverse direction, i.e. circumference direction, in each instance.

FIG. 8A again shows the normal state. The transverse crosspieces 32 are configured to be relatively rigid, while the basic structure is resilient as the result of bending of the longitudinal crosspieces 36. Bending is accompanied by a gradual rotation of the longitudinal crosspieces 36 in the circumference direction, which takes place at the level of the circumference of the stent. In the event of increased compression, the diameter of the stent is reduced by means of the rotation of the longitudinal crosspieces 36, up to the state of significant compression, which is shown in FIG. 8B. This state can be characterized as hard, since the elasticity of the lever arm (longitudinal crosspiece) 36 decreases with an increase in the angle of rotation. Therefore, the more the lever arm 36 turns in the transverse or circumference direction, the less resilience it still has. Once the rotation of the longitudinal crosspiece 36 has proceeded to such an extent that the latter runs essentially extended in the transverse direction, further resilience can only occur by bending the transverse crosspieces 32, but these have a clearly greater spring constant than the longitudinal crosspieces 36.

In FIGS. 8C and 8D, two possible embodiments of the stent shown in FIGS. 8A-D in the crimped state are shown, in which the stent has an even smaller diameter than in the state of significant compression. The states shown are achieved by such significant bending of the transverse crosspieces 32 that these are configured essentially in circular shape. In this connection, it should be noted that the length of the longitudinal crosspiece 36 is smaller than (length of the transverse crosspiece 32)/π, since otherwise, the crimped states shown in FIGS. 8C and 8D cannot be implemented.

From the above exemplary embodiments, particularly from the exemplary embodiment explained using FIGS. 8A-D, a general principle of the present endoprosthesis according to the invention becomes evident. The basic structure is preferably configured in such a manner that two design elements having different bending rigidity are combined with one another, specifically in such a manner that in the event of small stresses in the normal state, stress is exerted predominantly on the softer element (e.g. in the exemplary embodiment explained in FIGS. 8-D, the longitudinal crosspiece 36) and in the event of greater stresses in the state of significant compression, on the harder element (e.g. in FIGS. 8A-D, the transverse crosspiece 32).

The transition between the two load ranges takes place, for example, in that the softer element is at first bent in the event of light compression, but in the event of increasing compression is increasingly turned into the circumference direction or transverse direction, so that a bending stress in the normal state makes a transition, continuously or discontinuously, in the state of significant compression, into a predominantly single-axis stress state (tensile stress or compression). Such a single-axis stress state leads to "harder" behavior than bending stress does.

In order to be able to demonstrate the behavior according to the invention, the ability of the element of the basic structure that is under tensile stress to withstand stress, in each instance, is at least 10 times as great under tensile stress than it is under bending stress.

Figure 9:
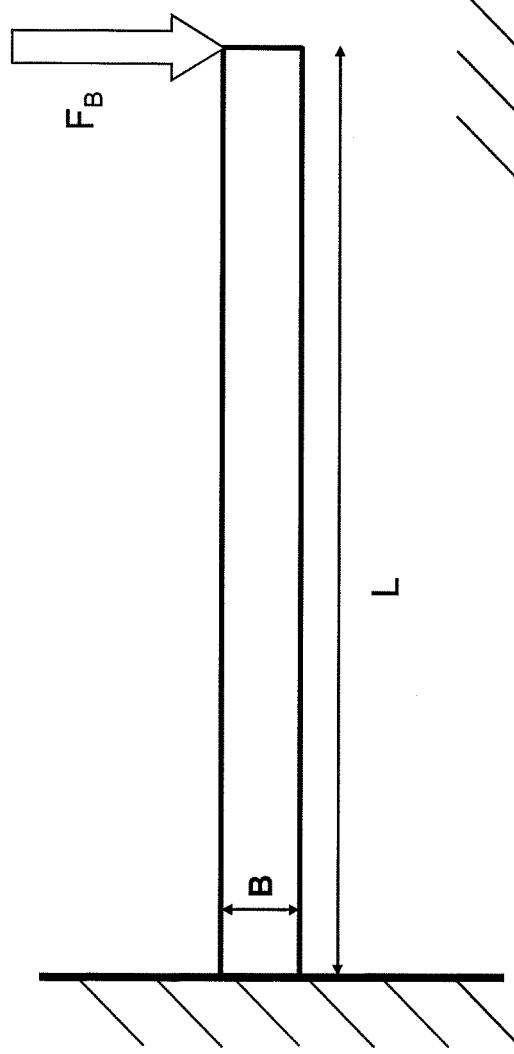
FIGS. 9 and 10 depict the progression of the forces that occur at the crosspieces.

Using the schematic drawings shown in FIGS. 9 and 10, it will be explained in the following that the requirement stated in the preceding paragraph can easily be achieved. In the pure bending of a crosspiece represented as a bar, shown in FIG. 9, a force $F_B$ acts transverse to the axis of the bar having the length L and the width B as well as the thickness D. In this connection, the thickness D is not shown in FIG. 9. This force determines a torque $M=F_B \cdot L$ that curves the bar, where the strongest curvature occurs at the clamping location (maximal torque at maximal distance from the engagement point of the force). Assuming that the relative extension and compression $\epsilon$ are distributed around a "neutral fiber" in the center of the bar, in linear and symmetrical manner, when bending occurs, the following applies for the counter-torque by the bar $$M = \int dy \int dz E \cdot \epsilon(y,z) \cdot y = \int dy \int dz E \cdot (\epsilon_{max} \cdot y / (B/2)) \cdot y = E \cdot \epsilon_{max} \cdot B^2/6 \cdot D,$$

i.e. for the permissible force $$F_B = M_{max}/L = E \cdot \epsilon_{max} \cdot B^2 \cdot 6 \cdot D/L = \epsilon_{max} \cdot E \cdot B \cdot D \cdot (B/6L).$$

In this connection, E refers to the modulus of elasticity, and $\epsilon_{max}$ refers to the maximal elastic extension of the material, and x/y/z refer to the directions along the length L/the width B/the thickness D of the non-stressed bar.

Figure 10:
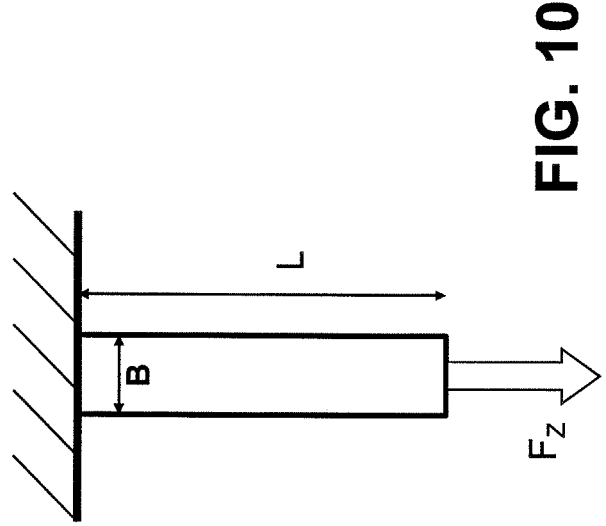

A pure tensile stress of a crosspiece simplified as a bar is shown in FIG. 10. A force $F_Z$ acts along the axis of a bar having the length L, the width B, and the thickness D. The related relative extension $\epsilon = \Delta L/L$ can be calculated from $\sigma = \epsilon \cdot E$ from the predetermined tensile stress $\sigma = F_Z/B \cdot D$ and the modulus of elasticity E of the material. The permissible force $$F_Z = \sigma_{max} \cdot B \cdot D = \epsilon_{max} \cdot E \cdot B \cdot D$$

is obtained from this.

Thus, the maximal tensile force $F_Z$ differs by a factor of 6L/B from the permissible bending force $F_B$. Since it holds true in practically all cases, for geometries such as those used for crosspieces of stents, that L>>B, the requirement $F_Z>10 \cdot F_B$ does not mean any restriction in the design, in all practical cases, but rather can be easily implemented.

Consequently, the basic structure shown in FIGS. 8A-D, for example, can easily be implemented in that the transverse brace 32 is more rigid than the longitudinal brace 36. This can be achieved, for example, very effectively by means of an adaptation of the crosspiece width B, which enters into the bending force squared (see calculation for FIG. 9). If, for example, ten times the force for bending of the transverse crosspiece 32 is to be implemented as that for bending of the longitudinal crosspiece 36 (at the same crosspiece length), then the width of the transverse crosspiece 32 must be dimensioned in such a way that it is greater by $\sqrt{10}$ times, in other words about 3.2 times than the width of the longitudinal crosspiece 36. The other dimensions of the crosspieces 32, 36 are the same. Such a variation in the crosspiece width can easily produced, for example, using the currently available methods of laser structuring.

Figure 11:
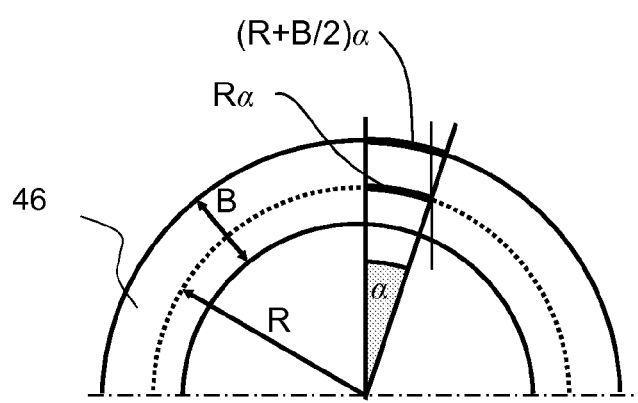
FIG. 11 depicts the elastic expansion of a crosspiece in the crimped state as compared to the expansion in the normal state.

Using FIG. 11, an elastic extension that is of importance for the crimped state will still be presented. In the crimped state, the bar (transverse crosspiece 32) must be maximally curved, in order to minimize the diameter of the stent. The orders of magnitude of the expansions that occur in this connection are evident from the sketch shown in FIG. 11. When a bar 46 having width B and having the radius R is bent, each piece of the outer contour is extended from its original length $R \cdot \alpha$ to the length $(R+B/2) \cdot \alpha$. The relative expansion is therefore $\epsilon = \Delta L/L = (B/2)/R$. In an idealized case of bending into a half-circle, the total length L of the bar precisely corresponds to $L = R \cdot \pi$. The material therefore must allow an expansion of $$\epsilon = (B/2)/R = (\pi/2) \cdot (B/L).$$

In the case of typical crosspiece geometries, the ratio B/L lies clearly below 1/10, so that this expansion lies on the order of magnitude of about 10%. Usual materials (316L, CoCr, also Mg) reach such values only by means of plastic deformation. This is not yet a fundamental reason for exclusion, in and of itself, but attention must be paid to ensure that in the event of this deformation (or complementarily, in the event of corresponding extension for dilatation), no forces occur that exceed the ability of the "weaker" element of the basic structure (e.g. longitudinal crosspiece 36) to withstand stress.

If a memory metal alloy, for example the material nitinol, is used as the material, then this deformation can be achieved solely by means of elastic expansion of the material of the basic structure, since the maximal elastic expansions of such material can reach the order of magnitude of 10%. Therefore the stent will demonstrate self-expanding behavior, i.e. crimping/dilatation do not impose any special requirements on the element (e.g. longitudinal crosspiece 36) in this regard. The use of a memory metal alloy as a basic material therefore appears to be advantageous in connection with the invention.

Using a quantitative finite-element analysis (FEM analysis), further details concerning implementation of the basic structures indicated can be clarified, which have an effect on the design of the endoprosthesis to be implemented, in each instance. Such practically relevant details are provided as follows.

It can be calculated, using the FEM analysis, whether narrower limits for stability result from the transient configurations of a basic structure element at the transition from bending stress to stretching stress.

Without additional stabilizing design elements, the design can tend to deform asymmetrically under stress, so that two adjacent elements jointly escape into a non-desired direction, e.g. jointly into the axial (possibly also radial) direction. It can be calculated, in detail, what further stabilization means (e.g. longitudinal connectors) are necessary to preclude this. Furthermore, it can be clarified whether it would be better to dispose adjacent segment rings with the same or opposite phase, or offset.

Furthermore, it can be determined from the calculations whether the elasticity range of nitinol or other shape memory metal alloys is sufficient for the functional scope according to the invention (if necessary with design adaptations).

It can be calculated in detail whether an S shape or a straight shape is more advantageous for elements of the basic structure in the crimped state.

Furthermore, it can be determined whether a curvature in a specific direction is more advantageous for elements of the basic structure in the normal state than a straight shape or a shape having a different curvature.

Furthermore, it should be calculated how the connection location between two crosspieces must be configured so that the stresses to be expected do not lead to local overload (material fatigue, micro-cracks).

Furthermore, it can be clarified, using the FEM calculations, whether implementation of the design according to the invention is fundamentally possible using conventional materials (316L, CoCr, Mg). In this connection, the question must be clarified whether the design can actually be implemented in such a manner that the elements of the basic structure can transfer a great tensile force not only in the event of compression, but also in the event of expansion. (This is a necessary prerequisite for the use of materials in which deformation of the element from the minimal ("crimped") to the ("expanded") normal state can fundamentally take place only plastically. Corresponding stents are not self-expanding but rather must be dilated using a balloon.)

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

REFERENCE SYMBOL LIST 5 longitudinal direction
10 crosspiece
11 inside
12 V-shaped notch
13 section of the side wall
14 notch
15 neck section
16 cylindrical section
18 notch
19 block-shaped section
21 contact element
25 step/depression
26 depression
30 longitudinal crosspiece
32 transverse crosspiece
34 restriction crosspiece
35 connection location
36 longitudinal crosspiece
37 connection location
40 transverse crosspiece
42 connection location
44 connector crosspiece
46 bar

What is claimed is:

1. Intraluminal endoprosthesis, having a basic structure configured in the shape of a hollow cylinder or a basic lattice, wherein in an expanded state, an inner volume enclosed by the basic structure is changeable by means of the elasticity of the basic structure, wherein the basic structure is configured to assume a normal state and a state of significant compression with regard to its compression behavior, wherein in the normal state a crosspiece runs in the longitudinal direction of the basic structure and is not taut and in the state of significant compression the basic structure is rigid and the crosspiece runs more transverse to the longitudinal direction and is taut, wherein the state of significant compression is characterized by the fact that an inside diameter threshold value of the basic structure amounting to about 75% compared to the inside diameter in the normal state is not reached or that a compression pressure threshold value from between about 0.2 bar to about 0.075 bar is exceeded.

2. Endoprosthesis according to claim 1, characterized in that forces introduced into the basic structure in the state of significant compression predominantly bring about a single-axis stress state of at least part of the basic structure.

3. Endoprosthesis according to claim 1, characterized in that the basic structure consists essentially of a shape memory metal alloy or nitinol.

4. Endoprosthesis according to claim 1, characterized in that the basic structure, in a crimped state, has an inside diameter that is significantly smaller than the inside diameter of the endoprosthesis in the state of significant compression.

5. Intraluminal endoprosthesis, having a basic structure configured in the shape of a hollow cylinder or a basic lattice, wherein in an expanded state, an inner volume enclosed by the basic structure is changeable by means of the elasticity of the basic structure, wherein the basic structure is configured to assume a normal state and a state of significant compression with regard to its compression behavior, wherein in the state of significant compression the basic structure is rigid, wherein the state of significant compression is characterized by the fact that an inside diameter threshold value of the basic structure amounting to about 75% compared to the inside diameter in the normal state is not reached or that a compression pressure threshold value from between about 0.2 bar to about 0.075 bar is exceeded, characterized in that the basic structure has transverse crosspieces that run essentially transverse to the longitudinal direction of the endoprosthesis and are preferably curved in the normal state, as well as longitudinal crosspieces that run essentially in the longitudinal direction, wherein the transverse crosspieces and the longitudinal crosspieces are connected with one another and disposed alternately one behind the other transverse to the longitudinal direction of the endoprosthesis, wherein a restriction crosspiece, in each instance, is disposed parallel to a transverse crosspiece, between each of two connection locations, which crosspiece, in the state of significant compression, counteracts a further increase in the radius of curvature of the transverse crosspiece if the radius of curvature of the crosspiece lies above a specific, predefined radius of curvature threshold value.

6. Endoprosthesis according to claim 5, wherein the restriction crosspiece is taut during the state of significant compression.

7. Endoprosthesis according to claim 6, characterized in that the elastic resistance of the basic structure in the state of significant compression amounts to at least ten times the elastic resistance of the basic structure in the normal state.

8. Endoprosthesis according to claim 6, characterized in that the transition from the elasticity in the normal state to the elasticity in the state of significant compression proceeds continuously.

9. The endoprosthesis according to claim 5, characterized in that the basic structure comprises a shape memory alloy or nitinol.

10. Endoprosthesis according to claim 5, characterized in that the basic structure, in a crimped state, has an inside diameter that is smaller than the inside diameter of the endoprosthesis in the state of significant compression.

11. Intraluminal endoprosthesis, having a basic structure configured in the shape of a hollow cylinder or a basic lattice, wherein in an expanded state, an inner volume enclosed by the basic structure is changeable by means of the elasticity of the basic structure, wherein the basic structure is configured to assume a normal state and a state of significant compression with regard to its compression behavior, wherein in the state of significant compression the basic structure is rigid, wherein the state of significant compression is characterized by the fact that an inside diameter threshold value of the basic structure amounting to about 75% compared to the inside diameter in the normal state is not reached or that a compression pressure threshold value from between about 0.2 bar to about 0.075 bar is exceeded, characterized in that the basic structure is formed by transverse crosspieces and restriction crosspieces that are alternately disposed one behind the other in the direction transverse to the longitudinal direction of the endoprosthesis and are connected with one another, wherein the transverse crosspieces, in the normal state, run essentially transverse to the longitudinal direction, and the restriction crosspieces, in the normal state, run essentially in the longitudinal direction of the endoprosthesis, wherein the restriction crosspieces can be rotated, with increasing compression, in such a manner that they increasingly run transverse to the longitudinal direction, wherein the elasticity of the restriction crosspieces decreases with increasing rotation, wherein in the normal state, the spring constant a of the transverse crosspieces is greater than the spring constant b of the restriction crosspieces, preferably a>10·b, and in the state of significant compression, the tensile strength of the restriction crosspieces is greater than the force required to bend the transverse crosspieces.

12. The endoprosthesis according to claim 11, characterized in that the basic structure comprises a shape memory alloy or nitinol.

13. Endoprosthesis according to claim 11, characterized in that the basic structure, in a crimped state, has an inside diameter that is smaller than the inside diameter of the endoprosthesis in the state of significant compression.

14. The endoprosthesis according to claim 11, characterized in the restriction crosspiece is taut during the state of significant compression.

15. The endoprosthesis according to claim 11, characterized in that the elastic resistance of the basic structure in the state of significant compression amounts to at least ten times the elastic resistance of the basic structure in the normal state.

16. Intraluminal endoprosthesis, having a basic structure configured in the shape of a hollow cylinder or a basic lattice, wherein in an expanded state, an inner volume enclosed by the basic structure is changeable by means of the elasticity of the basic structure, wherein the basic structure is configured to assume a normal state and a state of significant compression with regard to its compression behavior, wherein in the state of significant compression the basic structure is reduced as compared with the elasticity in the normal state, wherein the state of significant compression is characterized by the fact that an inside diameter threshold value of the basic structure amounting to about 75% compared to the inside diameter in the normal state is not reached or that a compression pressure threshold value from between about 0.2 bar to about 0.075 bar is exceeded, characterized in that the basic structure has transverse crosspieces that run essentially transverse to the longitudinal direction of the endoprosthesis and are preferably curved in the normal state, as well as longitudinal crosspieces that run essentially in the longitudinal direction, wherein the transverse crosspieces and the longitudinal crosspieces are connected with one another and disposed alternately one behind the other transverse to the longitudinal direction of the endoprosthesis, wherein a restriction crosspiece, in each instance, is disposed parallel to a transverse crosspiece, between each of two connection locations, which crosspiece, in the state of significant compression, counteracts a further increase in the radius of curvature of the transverse crosspiece if the radius of curvature of the crosspiece lies above a predefined radius of curvature threshold value.

17. The endoprosthesis according to claim 16, characterized in that the basic structure comprises a shape memory alloy or nitinol.

18. Endoprosthesis according to claim 16, characterized in that the basic structure, in a crimped state, has an inside diameter that is smaller than the inside diameter of the endoprosthesis in the state of significant compression.

19. The endoprosthesis according to claim 16, characterized in the restriction crosspiece is taut during the state of significant compression.

20. The endoprosthesis according to claim 16, characterized in that the elastic resistance of the basic structure in the state of significant compression amounts to at least ten times the elastic resistance of the basic structure in the normal state.

* * * * *